(12) United States Patent
Connors et al.

(10) Patent No.: US 7,430,274 B2
(45) Date of Patent: Sep. 30, 2008

(54) XRF ANALYZER

(75) Inventors: Brendan Connors, Somerville, MA (US); Brad Hubbard-Nelson, Concord, MA (US); Don Sackett, Bedford, MA (US)

(73) Assignee: Innov-X-Systems, Inc., Woburn, MA (US)

( * ) Notice: Subject to any disclaimer, the term of this patent is extended or adjusted under 35 U.S.C. 154(b) by 0 days.

(21) Appl. No.: 11/711,242

(22) Filed: Feb. 27, 2007

(65) Prior Publication Data

US 2008/0205592 A1   Aug. 28, 2008

(51) Int. Cl.
*G01N 23/223* (2006.01)
*G21K 4/00* (2006.01)
*G21K 3/00* (2006.01)
*H05G 1/10* (2006.01)

(52) U.S. Cl. .......................... 378/44; 378/42; 378/102; 378/156

(58) Field of Classification Search .................. 378/42, 378/44, 145, 156–160, 102, 70
See application file for complete search history.

(56) References Cited

U.S. PATENT DOCUMENTS

| | | | |
|---|---|---|---|
| 5,204,888 A * | 4/1993 | Tamegai et al. ............... 378/53 |
| 6,477,227 B1 | 11/2002 | Kaiser et al. |
| 6,501,825 B2 | 12/2002 | Kaiser et al. |
| 6,850,592 B2 | 2/2005 | Schramm et al. |
| 6,909,770 B2 | 6/2005 | Schramm et al. |

* cited by examiner

*Primary Examiner*—Irakli Kiknadze
(74) *Attorney, Agent, or Firm*—Iandiorio Teska & Coleman

(57) ABSTRACT

An XRF system, preferably handheld, includes an X-ray source for directing X-rays to a sample, a detector responsive to X-rays emitted by the sample, and a filter assembly with multiple filter materials located between the X-ray source and the detector. An analyzer is responsive to detector and is configured to analyze the intensities of X-rays irradiated by the sample at one power setting and to choose a filter material which suppresses certain intensities with respect to other intensities. A device, controlled by the analyzer, automatically moves the filter assembly to the chosen filter material and then the analyzer increases the power setting to analyze certain non-suppressed intensities.

16 Claims, 7 Drawing Sheets

XRF ANALYZER

FIELD OF THE INVENTION

This subject invention relates to X-ray fluoroscopy techniques and systems.

BACKGROUND OF THE INVENTION

X-ray fluoroscopy (XRF) is a technique used to detect elements present in a sample. An X-ray tube is typically used as a source of X-rays directed to the sample. A detector is responsive to the X-rays emitted (e.g., scattered) from the sample. An analyzer processes the output signals produced by the detector and divides the energy levels of the detected X-ray photons into several energy subranges by counts of the number of X-ray photons detected to produce a graph depicting the X-ray spectrum of the sample.

Handheld XRF analyzers are well known. See the applicants' website at www.innov-x-sys.com. See also U.S. Pat. Nos. 6,501,825; 6,909,770; 6,477,227; and 6,850,592. Using a handheld XRF analyzer, an inspector can determine, for example, whether lead is present in paint on a wall in a house, apartment, school, or other building.

In another example, The European Union has issued a directive called RoHs (Restriction on the Use of Certain Hazardous Substances). This directive restricts the use of certain hazardous substances (e.g., chromium) in electrical and electronic equipment. In still another example, a refineries require a certain grade stainless steel to be used including 0.2%-0.4% titanium.

State of the art XRF devices provide sufficient energy resolution, testing times of a few minutes or less, are powered by batteries, and obtain high X-ray count rates. The best available detector technology that can be used in conjunction with a handheld device to achieve good energy resolution, however, is a silicon PiN diode detector typically with Peltier cooling. This specific detector is limited in maximum count rate such that without special primary beam filtering, it cannot meet the required detection limits and precisions in all cases.

Without filtering the X-ray beam from the source, the maximum count rate of the Si PiN detector is often exceeded and low concentrations of elements such as hazardous substances cannot be reliably detected in a sample.

Filters are known in laboratory based XRF systems typically operated by scientists. For handheld XRF systems used by non-scientists, filters are typically not used or require the user to choose the specific filter material to be placed in front of the X-ray source.

Thus, it would be advantageous to have a handheld XRF device which can be reliably used by an inspector in the field to detect the presence of hazardous substances and other substances.

SUMMARY OF THE INVENTION

It is therefore an object of this invention to provide a more reliable and more accurate handheld XRF analyzer.

It is a further object of this invention to provide such an analyzer which is able to detect the concentration of many different substances without exceeding the maximum count rate of the detector.

It is a further object of this invention to provide such an analyzer which can be used to ensure compliance with the RoHs and other directives.

It is a further object of this invention to provide such an analyzer which is cost effective to manufacture and simple to use.

It is a further object of this invention to provide a new method of analyzing samples.

The subject invention results from the realization that a hand held XRF device can be operated at a much higher tube power than normal and the maximum count rate of a Si PiN detector can be prevented from being exceeded when attempting to detect the presence of a particular low concentration element in a sample with other predominant elements by automatically analyzing the sample at one X-ray tube current setting, noting the X-ray intensity of a large concentration element, and suppressing that intensity by moving a filter wheel to block a source X-ray intensity which would be emitted by the large concentration element. Then, the X-ray tube current setting can be increased to analyze the low concentration element.

The subject invention, however, in other embodiments, need not achieve all these objectives and the claims hereof should not be limited to structures or methods capable of achieving these objectives.

One preferred XRF system, preferably configured to be handheld, in accordance with the subject invention, features an X-ray source for directing X-rays to a sample, a detector responsive to X-rays emitted by the sample, and a filter assembly with multiple filter materials located between the X-ray source and the detector. An analyzer is responsive to detector and configured to analyze the intensities of X-rays emitted by the sample. Based on this analysis, the analyzer chooses a filter material which suppresses certain intensities with respect to other intensities. A device, controlled by the analyzer, moves the filter assembly to the chosen filter material in an automatic fashion.

In the preferred embodiment, the detector is a silicon PiN diode detector. Typically, the filter assembly is configured as a filter wheel located in front of the X-ray source. Typical filter materials include iron, copper, aluminum, and tin. The filter assembly may include an X-ray blocking material for safety.

In one example, the filter wheel includes a circumferential gear and the device includes a mating gear driven by a motor controlled by the analyzer to rotate the filter wheel.

In one example, the analyzer is programmed to detect high intensities of copper emitted by the sample and to choose a copper filter material to enhance the intensity of Cadmium with respect to copper detected by the detector. In another example, the analyzer is programmed to detect high intensities of iron emitted by the sample and to choose an iron filter material to enhance the intensities of chromium with respect to aluminum detected by the detector. In still another example, the analyzer is programmed to detect high intensities of tin irradiated by the sample and to choose a tin filter material to enhance the intensities of cadmium with respect to tin detected by the detector. Also, the analyzer can be further configured to adjust the X-ray power based on the intensities of X-rays emitted by the sample and also the chosen filter material to further enhance certain intensities with respect to other intensities.

One handheld XRF system in accordance with this invention includes an X-ray source for directing X-rays to a sample, a Si PiN detector responsive to X-rays emitted by the sample, and a filter assembly with multiple filter materials located between the X-ray source and the detector. An analyzer is responsive to the detector and is configured to analyze the intensities of X-rays emitted by the sample and to choose a filter material which ensures the maximum count rate of the Si PiN detector is not exceeded. A device is responsive to the analyzer for moving the filter assembly to the chosen filter material.

One method of analyzing a sample in accordance with this invention features directing X-rays to the sample at a predetermined beam setting, detecting X-rays emitted by the sample, analyzing the X-rays, based on the analysis, automatically adjusting the beam setting and choosing a filter, directing X-rays to the sample at the adjusted beam setting and through the filter, and again analyzing the X-rays.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
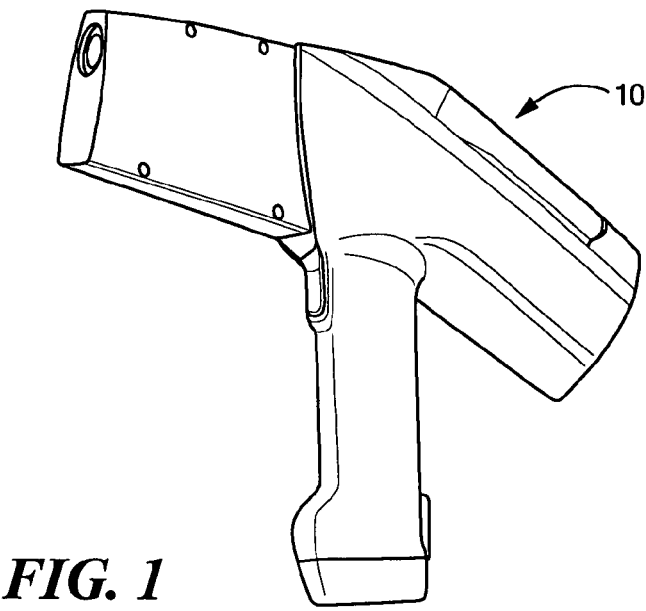
FIG. 1 is a schematic three-dimensional view of a typical handheld XRF analyzer.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

One preferred version of a handheld XRF analyzer in accordance with this invention is shown at 10 in FIG. 1. The primary components of analyzer 10 include controllable X-ray source 12, FIG. 2 powered by power source 14 (typically including a rechargeable battery pack), detector 16 (typically a Si PiN detector) and filter assembly 18 including filter wheel 20 with multiple filter materials 22a-22e located in front of X-ray source 12. Analyzer 24, typically a programmed processor or controller or similar circuitry, is responsive to detector 16 and is configured to analyze the intensities of X-rays irradiated by the sample and to choose a particular filter material which enhances certain intensities with respect to other intensities. Device 26 is controlled by analyzer 24 and moves filter wheel 20 to orient the chosen filter material in front of X-ray source 12. The filter materials 22a-22e can be iron, copper, aluminum, tin, and others and also a blocking material such as lead. The analyzer 24 may be programmed to orient the lead filter in front of X-ray source 12 as a default for safety reasons.

In this way, the inherent limitations of a Si PiN diode are overcome by using a multi-position filter wheel and specially chosen filter materials to suppress intensities from large concentration elements, for example base elements in alloys and bromine in certain plastics. The current supplied to the controllable X-ray tube current can be ramped up to achieve the required precision without overwhelming the PiN diode detector. Exemplary applications include measuring Cadmium in concentrations of less than 100 ppm in alloys and in tin-based solders, measuring chromium in concentrations of less than 250 ppm in iron-based alloys, and the like. A minimum of four filter positions are possible, preferably there are five, and the filter materials can be chosen to meet RoHS detection limits by using a handheld device. The detection limits and precision required for this application when a PiN diode detector is used is not exceeded and the X-ray tube need not be run at higher outputs which would overcome the PiN diode detector count rate limitations. The multiple filter design wherein a particular filter material is automatically placed in front of the X-ray tube suppresses the most intense elements and brings out low concentrations of other elements more effectively.

Figure 3:
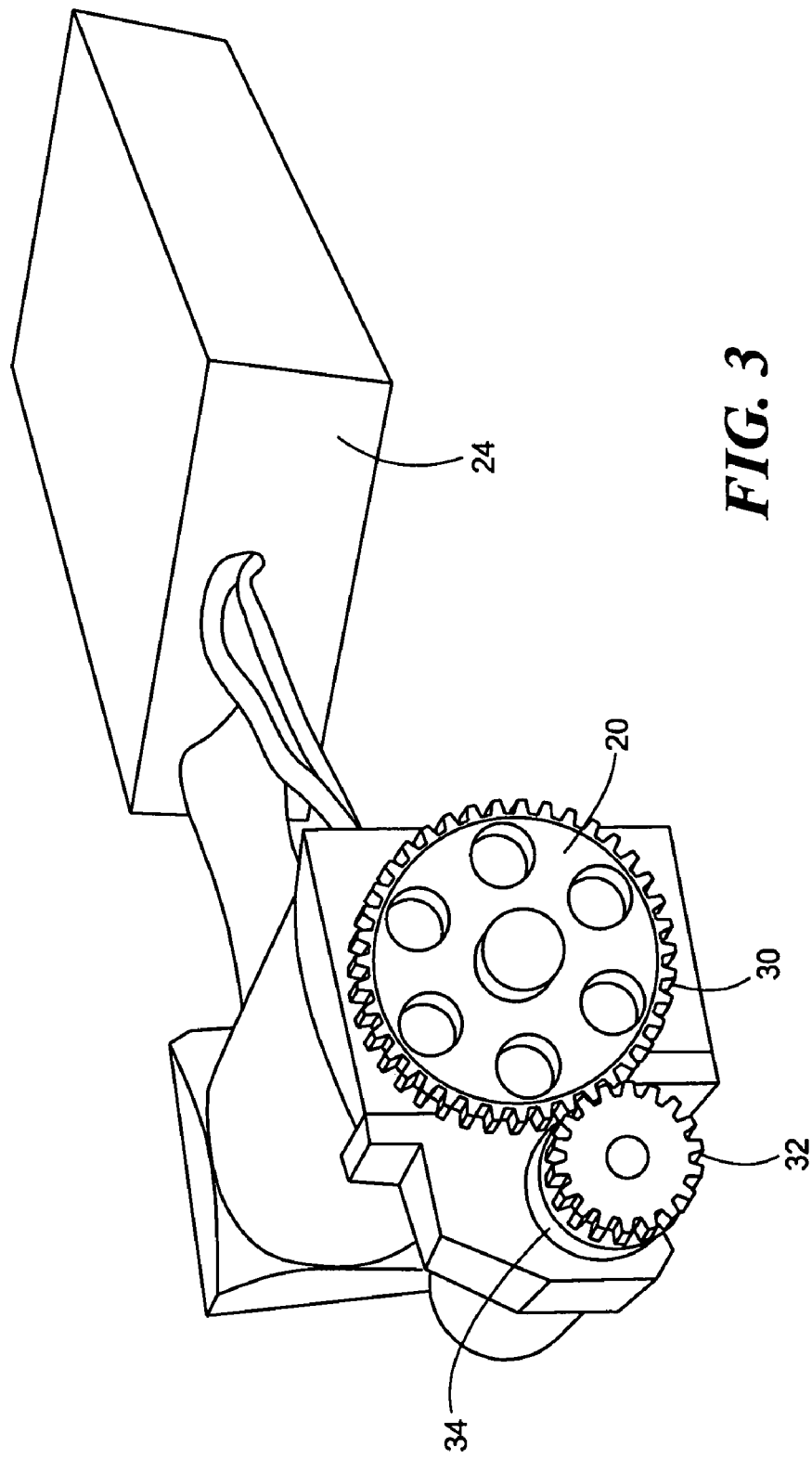
FIG. 3 is a schematic three-dimensional view showing a few of the primary components associated with the handheld XRF analyzer shown in FIG. 2.
Figure 4:
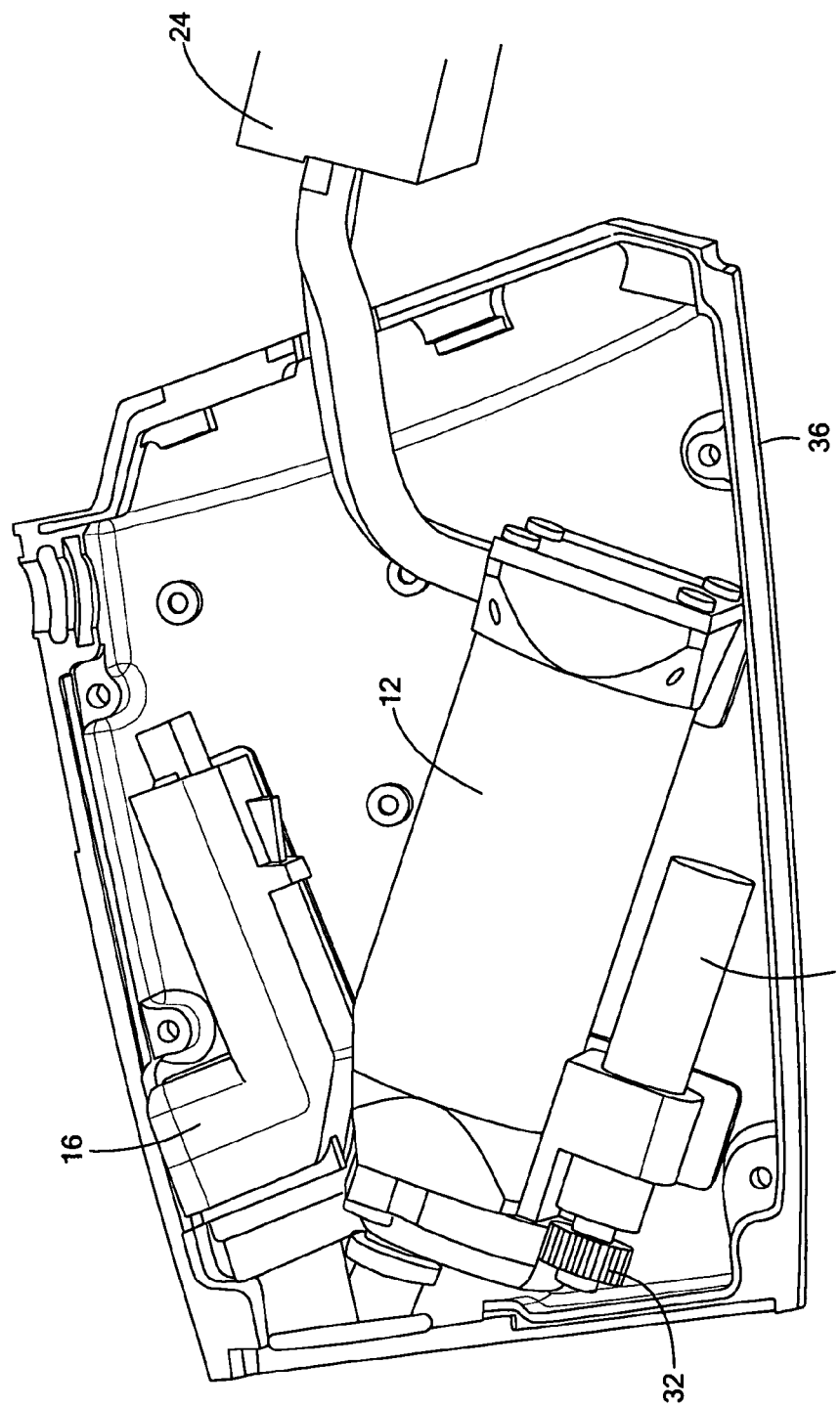
FIG. 4 is a schematic three-dimensional top view showing the components of the XRF analyzer shown in FIG. 3 inside an analyzer casing.
Figure 5:
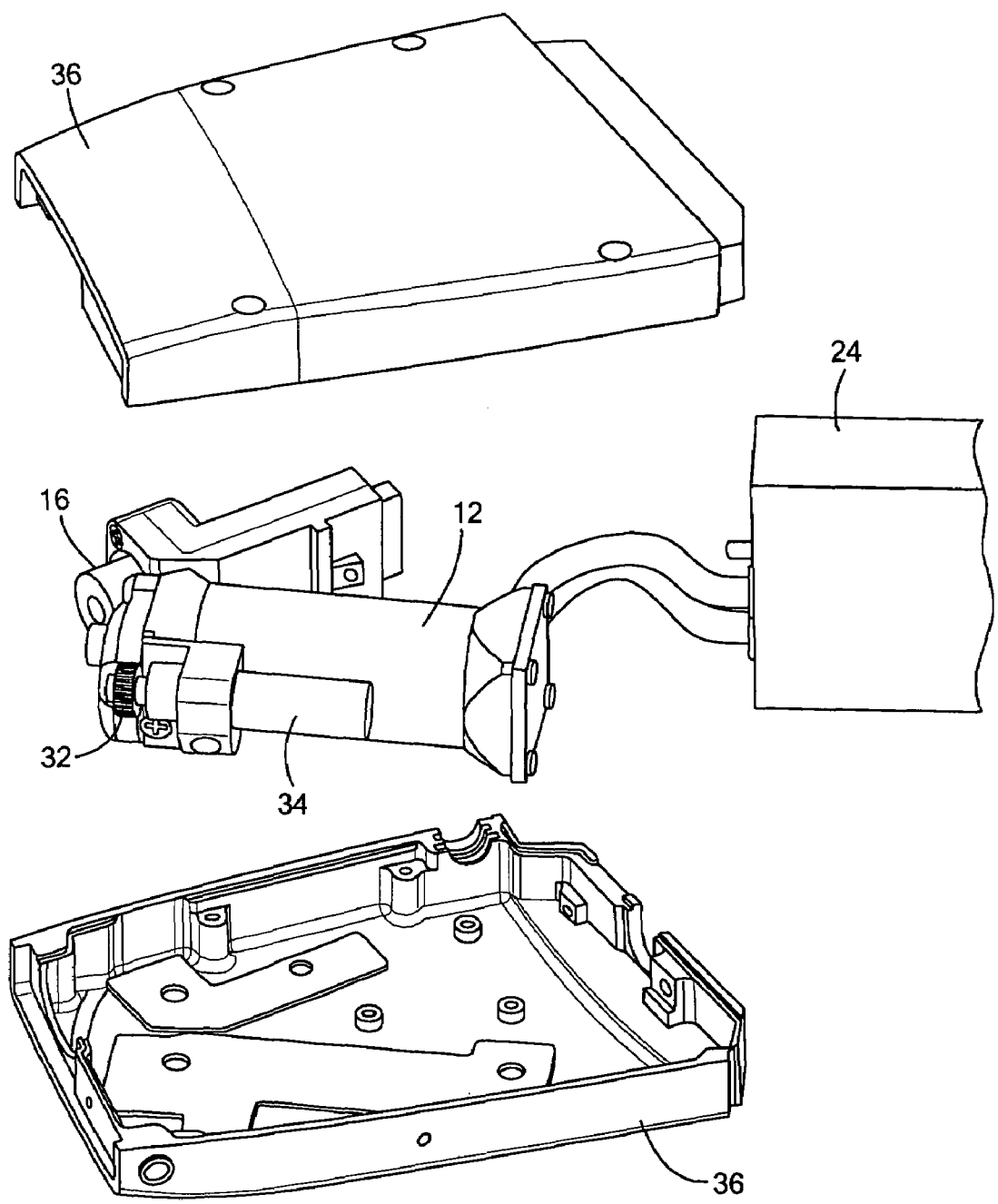
FIG. 5 is a schematic three-dimensional side-exploded view showing again several of the primary components associated with a preferred embodiment of an XRF analyzer in accordance with the subject invention.

FIG. 3 shows a prototype version of filter wheel 20 in more detail. Filter wheel 20 includes circumferential gear 30. Mating gear 32 is driven by motor 34 controlled by analyzer 24 to rotate filter wheel 20 via gear 30 which meshes with gear 32. Motor 34 is typically a step or servo motor and optical or other encoder techniques can be used to provide the analyzer with the current position of the filter wheel and to move the filter wheel to place the appropriate filter material in front of the X-ray tube. FIGS. 4-5 also show one possible arrangement of motor 34, gear 32, and the relative positions of detector 16, X-ray tube 12 and analyzer 24 with respect to handheld XRF analyzer case 36.

The analyzer can be configured (e.g., programmed) in a variety of ways to automatically adjust the position of the filter wheel. For example, the analyzer can be programmed to detect high intensities of copper irradiated by a sample and to then choose a copper filter material to enhance the intensity of Cadmium with respect to copper in the spectrum detected by the detector. The analyzer can be programmed to detect high intensities of iron irradiated by the sample and to then choose an iron filter material to enhance the intensities of chromium with respect to iron in the spectrum detected by the detector. The analyzer can be programmed to detect high intensities of tin irradiated by the sample and to then choose a tin filter material to enhance the intensities of cadmium with respect to tin in the spectrum detected by the detector.

Figure 2:
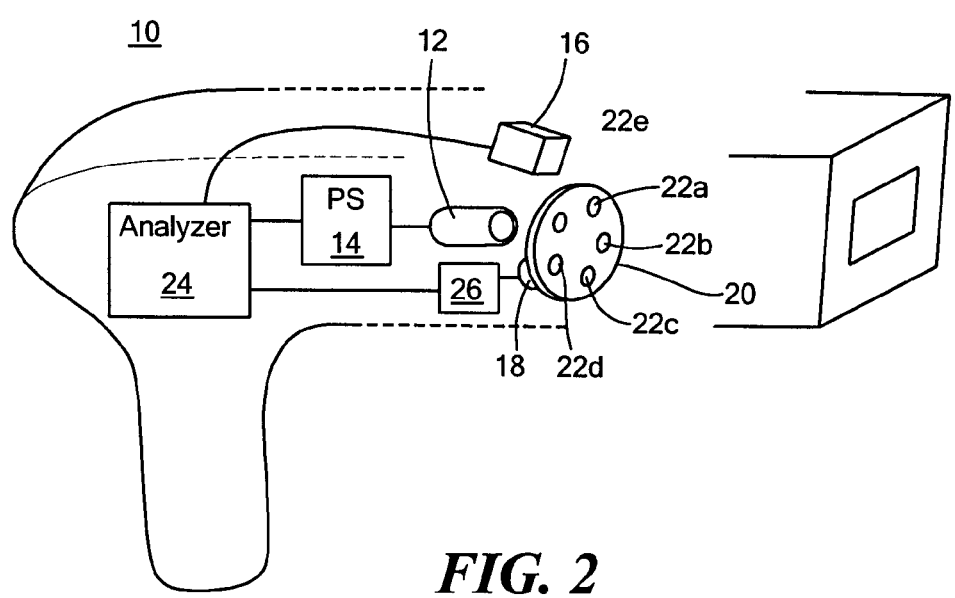
FIG. 2 is a highly schematic partially cut-away view of one preferred version of a handheld XRF analyzer in accordance with the subject invention.

Also, based on the intensities of the X-rays emitted by the sample and the chosen filter wheel material, the analyzer can be programmed to adjust the output of power source 14, FIG. 2 to vary the X-ray beam settings of the X-ray source.

Figure 6:
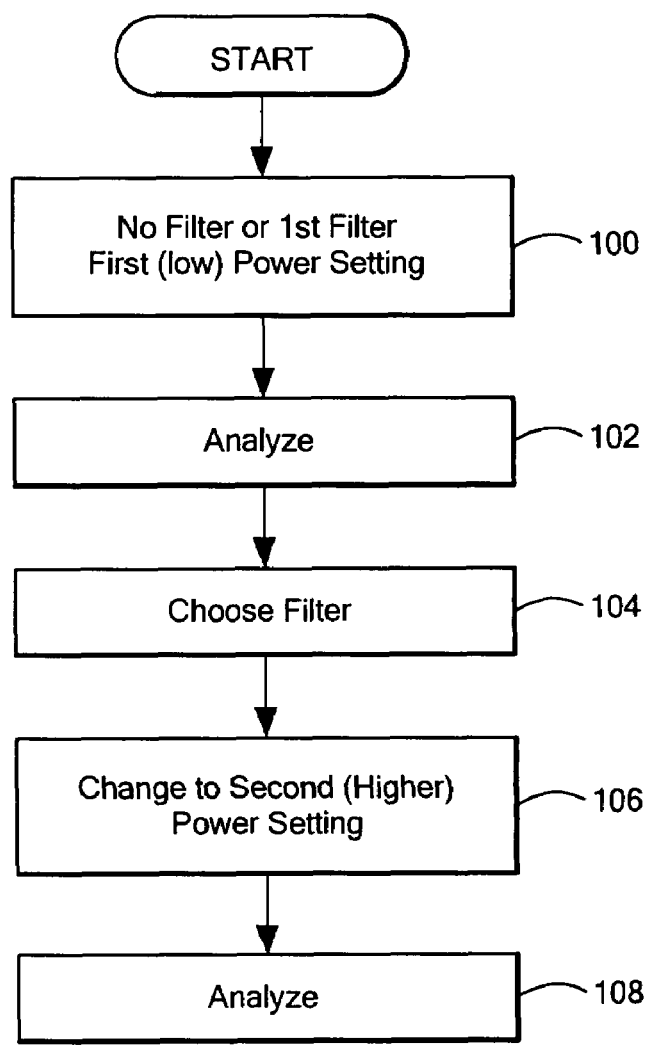
FIG. 6 is a flow chart depicting the primary steps associated with one preferred method of analyzing a sample in accordance with the subject invention.

As shown in FIG. 6, step 100, analyzer 24, FIG. 2, upon initialization or reset, rotates filter wheel 20 so that a standard or a first filter (e.g., a 2 mm aluminum filter) is in front of source 12. Analyzer 24 also controls power source 14 to set the power (e.g., current) supplied to X-ray source 12 to be at a first setting, in one example, 40 kV at 10 μA. The X-ray spectrum of the sample is then analyzed, step 102, FIG. 6. In one example, high concentrations (50% or more) or copper are detected. But, the system cannot accurately detect lower concentrations of cadmium (e.g., less than 70 ppm in less than 30 sec), for example. Were the current supplied to the X-ray source increased in order to analyze lower concentration of cadmium more quickly, the limit of detector 16, FIG. 2 would be exceeded and its performance would begin to degrade. So, in the subject invention, analyzer 24 chooses a filter material, step 104, FIG. 6 which suppresses, in this specific example, the copper X-rays. Analyzer 24, FIG. 3 thus controls motor 34 to rotate filter wheel 20 until a copper filter is located in front of the X-ray source, step 106, FIG. 6. Now, analyzer 24 controls power source 14 to ramp up the current supplied to X-ray source 12 until a new second power setting is reached (e.g., 40 kV at 70 µA) as selected by analyzer 24. Although this second power setting may be as much as five times the initial power setting, because of the chosen filter, the limit of the detector is not exceeded. In this way, at step 108, FIG. 6 the X-ray source is able to increase the limit of detection of cadmium in the sample without performance degradation of the sensor. And, now the cadmium in the sample can be analyzed by the analyzer. In one example, the limit of detection of cadmium was improved by a factor of two (or more).

Figure 7:
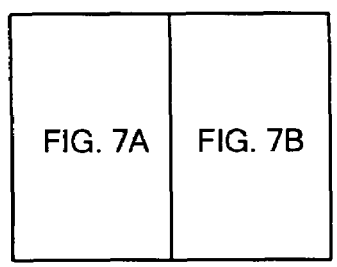
FIG. 7 is a flow chart depicting, in more detail, the primary steps associated with one method of analyzing a sample in accordance with the subject invention.
Figure 7A:
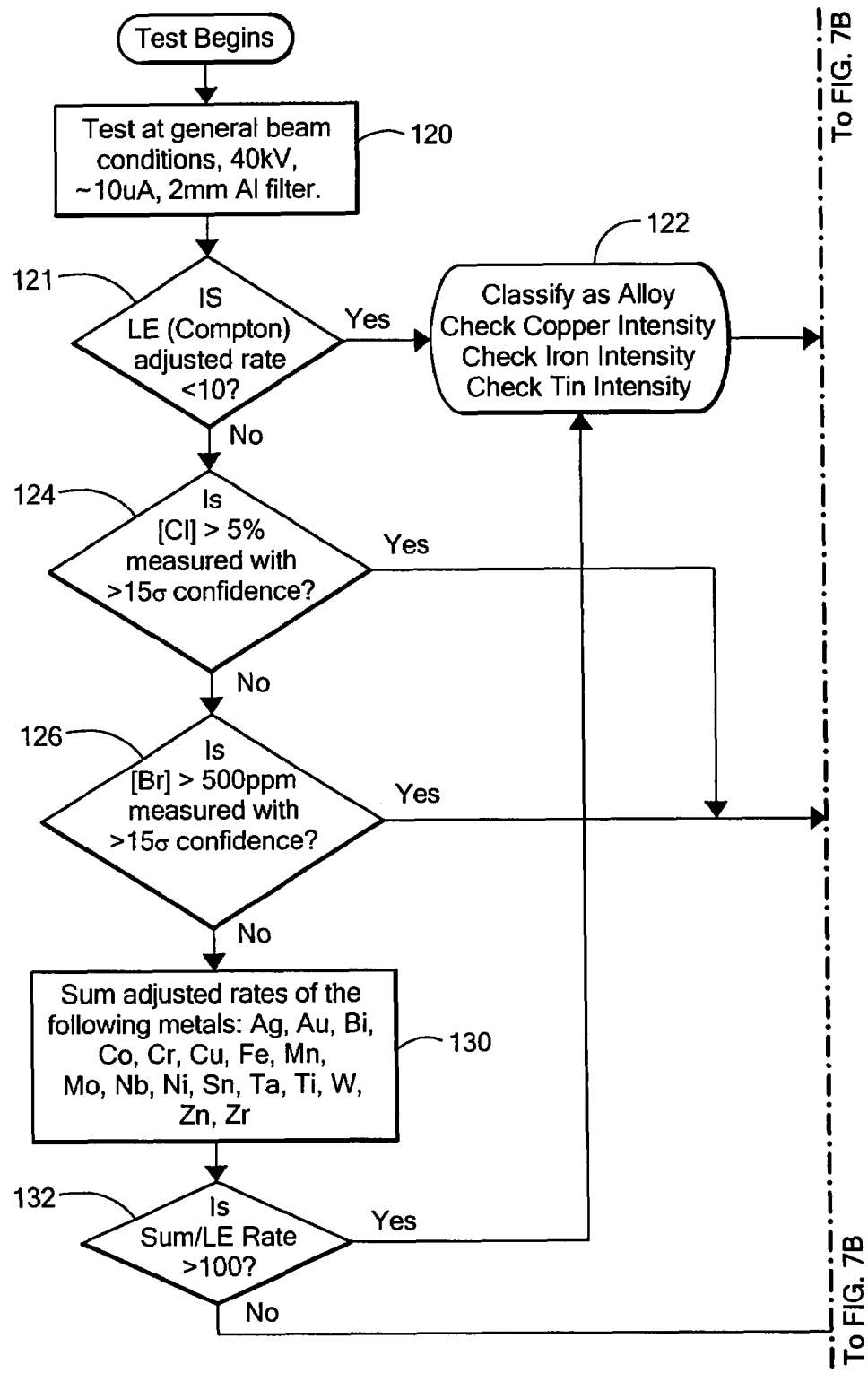
Figure 7B:
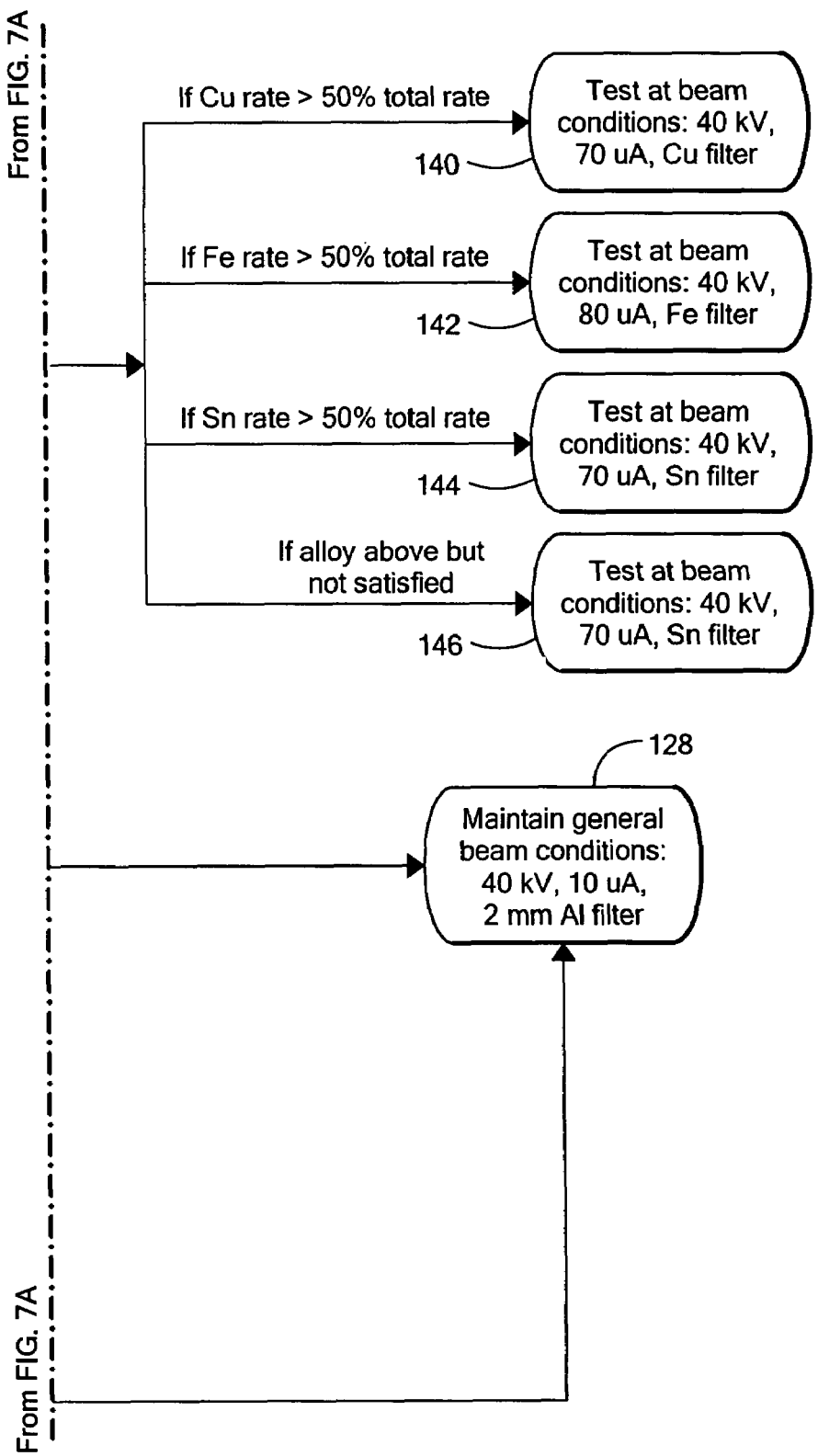

FIG. 7 shows how the filter assembly and power source are first set at general beam conditions, 40 kV, 10 µA, and a 2 mm aluminum filter is used, step 120. The elemental intensities are detected using these general beam conditions and filter. The analyzer then determines whether the scattered X-ray intensity is less than a threshold, e.g., whether the LE (Compton) adjusted rate is less than 10. This test is to discern a low density sample such as a polymer-plastic sample from a high density material like an alloy by the amount of scattered X-rays from the sample being tested. X-rays are much more likely to be scattered by low density materials and much more likely to be absorbed (and yield fluorescence) from alloys. So the LE rate and Compton are terms for scattered radiation. The scattered intensity is analyzed to make a preliminary decision as to whether the sample is a polymer or an alloy. If the LE rate and Compton scattering adjusted rate is greater than 10, then the analyzer controls the power source to change to a setting of 40 kV, 70 µA and controls the filter assembly to choose a transition metal filter, step 122. Otherwise, next the scattered intensity is analyzed for the presence of chlorine, step 124 and bromine, step 126 since the presence of these elements in the percentages or parts shown in step 124 and 126 typically indicate brominated (flame retardant) plastics and PVC. It is exceedingly rare to find bromine or chlorine in an alloy. Thus, if chlorine or bromine are present as shown in step 124 and 126, it is likely that the sample is plastic and thus at step 128 the general beam conditions of step 120 are maintained. Otherwise, in step 130, the elemental intensities of certain metals from step 120 such as those shown in step 130 are summed and if the sum to the scattered X-ray intensity rate at step 132 is greater than 100 then a new beam conditions and filter shown at step 122 are chosen. Otherwise, the general beam conditions at step 128 are maintained.

The testing at alloy beam conditions in step 122 can then proceed further. If the copper rate is greater than 50% of the total rate, for example, the alloy can be tested at copper alloy beam conditions, for example at 40 kV, 70 µA with a copper filter, step 140. If the iron rate is greater than 50% of the total rate, the alloy is tested at 40 kV, 80 µA with an iron filter material chosen by the analyzer, step 142. If the rate of tin is greater than 50% of the total rate, the power source is controlled for 40 kV, 70 µA beam conditions with a tin filter, step 144. In all other cases, the beam conditions can be set to 40 kV, 70 µA, also with the copper filter, step 146.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. An XRF system comprising:
   an X-ray source for directing X-rays to a sample;
   a power source for the X-ray source;
   a detector responsive to X-rays emitted by the sample;
   a filter assembly with multiple filter materials located between the X-ray source and the detector;
   an analyzer responsive to detector and configured to:
      analyze the intensities of X-rays emitted by the sample at a first power setting of the X-ray source,
      choose a filter material which suppresses certain intensities with respect to other intensities, and
      control the power source to change the first power setting to a second power setting to improve the limit of detection of the system; and
   a device, controlled by the analyzer, for moving the filter assembly to the chosen filter material.

2. The system of claim 1 in which the detector is a silicon PiN diode detector.

3. The system of claim 1 in which the filter assembly is a filter wheel located in front of the X-ray source.

4. The system of claim 3 in which the filter wheel includes a circumferential gear and the device includes a mating gear driven by a motor controlled by the analyzer to rotate the filter wheel.

5. The system of claim 1 in which the filter materials are selected from the group consisting of iron, copper, aluminum, and tin.

6. The system of claim 1 in which the filter assembly includes an X-ray blocking material for safety.

7. The system of claim 1 in which the analyzer is programmed to detect high intensities of copper emitted by the sample and to choose a copper filter material to enhance the intensity of Cadmium with respect to copper detected by the detector.

8. The system of claim 1 in which the analyzer is programmed to detect high intensities of iron emitted by the sample and to choose an iron filter material to enhance the intensities of chromium with respect to iron detected by the detector.

9. The system of claim 1 in which the analyzer is programmed to detect high intensities of tin emitted by the sample and to choose a tin filter material to enhance the intensities of cadmium with respect to tin detected by the detector.

10. A handheld XRF system comprising:

an X-ray source for directing X-rays to a sample;

a Si PiN detector responsive to X-rays emitted by the sample;

a filter assembly with multiple filter materials located between the X-ray source and the detector;

an analyzer responsive to the detector and configured to analyze the intensities of X-rays emitted by the sample and to choose a filter material and power setting for the X-ray source which ensures the maximum count rate of the Si PiN detector is not exceeded.

11. A method of analyzing a sample, the method comprising:

directing X-rays to the sample at a predetermined beam setting;

detecting X-rays emitted by the sample;

analyzing the X-rays;

based on the analysis, automatically choosing a filter and a new beam setting;

directing filtered X-rays to the sample at the new beam setting; and again analyzing the X-rays.

12. An XRF system comprising:

an X-ray source for directing X-rays to a sample;

a detector responsive to X-rays emitted by the sample;

a filter assembly with multiple filter materials located between the X-ray source and the detector;

a device, controlled by an analyzer, for moving the filter assembly;

the analyzer configured to:

direct X-rays to the sample at a predetermined beam setting, detect X-rays emitted by the sample, analyze the X-rays and chose a filter material, based on the analysis, automatically chose a new beam setting and control the device to place the chosen filter material in the path of the X-rays, direct X-rays to the sample at the new beam setting and through the chosen filter, and again analyze the X-rays.

13. The system of claim 12 in which the detector is a silicon PiN diode detector.

14. The system of claim 12 in which the filter assembly includes a filter wheel located in front of the X-ray source.

15. The system of claim 14 in which the filter assembly includes an X-ray blocking material for safety.

16. The system of claim 14 in which the filter wheel includes a circumferential gear and the device includes a mating gear driven by a motor controlled by the analyzer to rotate the filter wheel.

* * * * *